(12) United States Patent
Balbo

(10) Patent No.: US 6,644,618 B1
(45) Date of Patent: Nov. 11, 2003

(54) FAST-FIT CLAMP FOR REGULATING FLOW ALONG FLEXIBLE TUBES, IN PARTICULAR FOR MEDICAL USE

(76) Inventor: Enrico Balbo, Via Monviso, 77, I-41100 Modena (IT)

( * ) Notice: Subject to any disclaimer, the term of this patent is extended or adjusted under 35 U.S.C. 154(b) by 0 days.

(21) Appl. No.: 09/980,704

(22) PCT Filed: Jun. 8, 2000

(86) PCT No.: PCT/IT00/00232
§ 371 (c)(1),
(2), (4) Date: Dec. 7, 2001

(87) PCT Pub. No.: WO00/77428
PCT Pub. Date: Dec. 21, 2000

(30) Foreign Application Priority Data

Jun. 10, 1999 (IT) .................... MO99A0129

(51) Int. Cl.⁷ .................... F16K 7/06; A61M 39/28
(52) U.S. Cl. .................... 251/10; 251/9
(58) Field of Search .................... 251/9, 10

(56) References Cited

U.S. PATENT DOCUMENTS

| | | | | | |
|---|---|---|---|---|---|
| 3,247,852 A | * | 4/1966 | Schneider | .................... | 251/10 |
| 3,698,681 A | * | 10/1972 | Lacey | .................... | 251/10 |
| 3,822,052 A | * | 7/1974 | Lange | .................... | 251/10 |
| 3,942,228 A | * | 3/1976 | Buckman et al. | .................... | 251/10 |
| 4,453,295 A | * | 6/1984 | Laszczower | .................... | 251/10 |
| 4,588,160 A | * | 5/1986 | Flynn et al. | .................... | 251/10 |
| 4,589,626 A | * | 5/1986 | Kurtz et al. | .................... | 251/10 |
| 5,203,056 A | * | 4/1993 | Funk et al. | .................... | 251/10 |
| 5,318,546 A | * | 6/1994 | Bierman | .................... | 251/10 |
| 6,113,062 A | * | 9/2000 | Schnell | .................... | 251/10 |
| 6,161,812 A | * | 12/2000 | Guala et al. | .................... | 251/10 |
| 6,196,519 B1 | * | 3/2001 | Utterberg | .................... | 251/10 |

* cited by examiner

Primary Examiner—Paul J. Hirsch
(74) Attorney, Agent, or Firm—Guido Modiano; Albert Josif; Daniel O'Byrne

(57) ABSTRACT

A fast-fit clamp for partly or fully closing flexible tubes, in particular for medical use, has a laminar body bent backwards on itself, fitted through longitudinally with a tube, and having two elastically competing ends between which project radially inwards two opposite transverse teeth for gripping the tube; at least two split through holes being formed in the laminar body, with openings facing outwards on opposite sides; and provision being made for centering means for centering the competing ends, and latch means for fastening the competing ends simply or gradually.

6 Claims, 1 Drawing Sheet

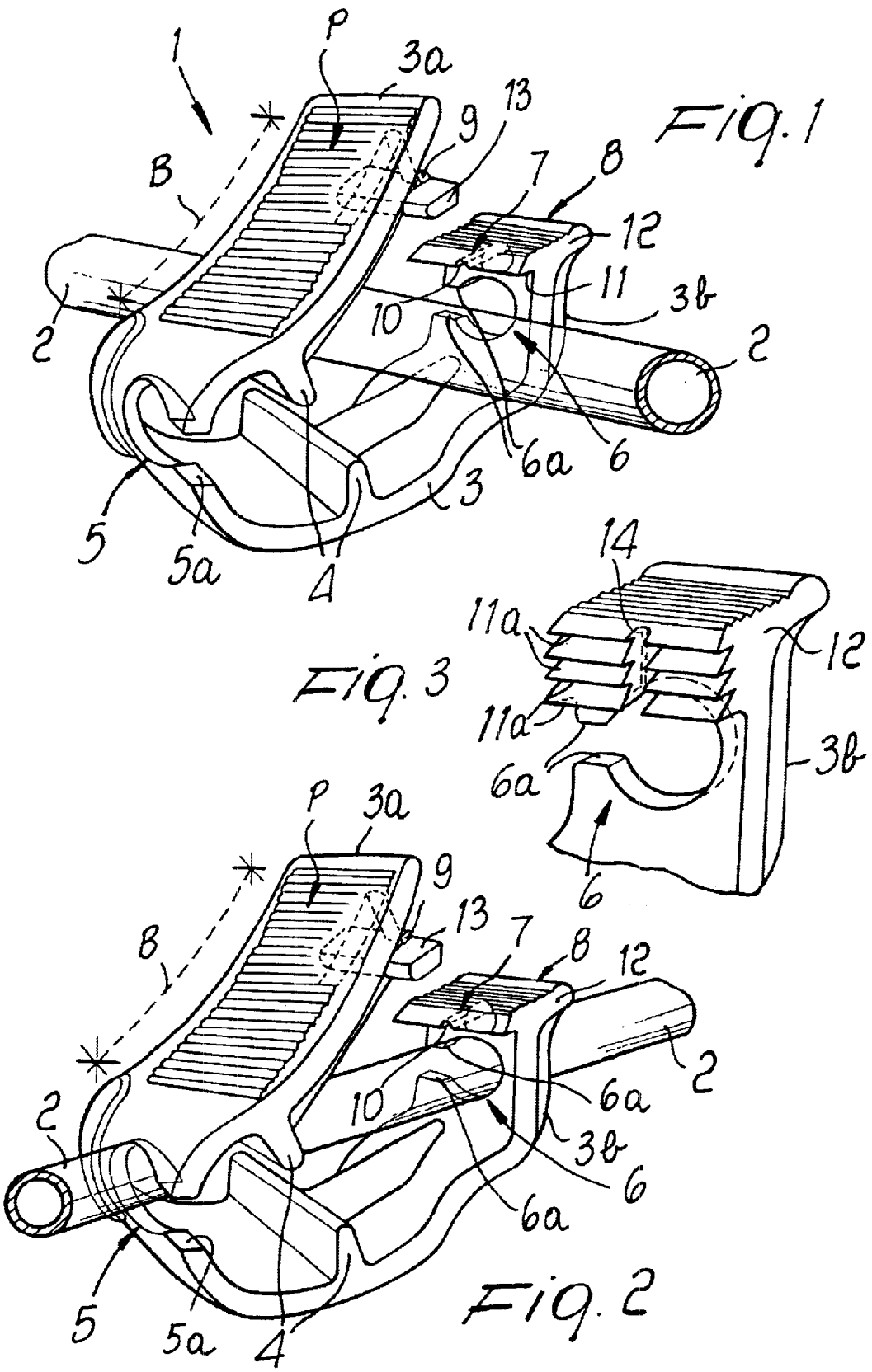

FAST-FIT CLAMP FOR REGULATING FLOW ALONG FLEXIBLE TUBES, IN PARTICULAR FOR MEDICAL USE

TECHNICAL FIELD

The present invention relates to a fast-fit clamp for regulating flow along flexible tubes, in particular for medical use.

BACKGROUND ART

Medical kits comprise various devices or so-called clamps, which, fitted at predetermined points along tubes, provide for reducing or cutting off the passage of blood or other physiological fluids, or for regulating the dosage or supply rate of drugs administered to patients.

Such clamps are normally supplied as part of the kits themselves, and, given the delicate nature of the field in which they are used, are sterilized and packed in sealed packages together with the kits, to ensure maximum sterility pending use.

Preassembly of the kits calls for fitting on the clamps before the kits are sterilized and packed, due to known clamps comprising a laminar body substantially bent backwards on itself and having at least two through holes—an input and output hole—closed peripherally and through which the tube is inserted; the tube is then pressed by a transverse tooth formed on the movable end of the laminar body, which is locked in the desired position by means of indentations formed on the opposite end.

Given the design. of known clamps, preassembly therefore calls for fitting the clamps to the tubes before other conventional devices, such as bags, fittings and similar, are fitted permanently or removably to the ends of the tubes.

The above state of the art leaves room for further improvement, by enabling the clamps to be fitted on after assembly as performed normally, and, during actual use of the kit, to be moved and used in positions other than that provided for initially by the maker.

Known devices also leave room for improvement in terms of fast, easy handling, to enable troublefree use by female medical personnel who are especially sensitive to, and frequently complain of, broken thumb nails when closing conventional clamps.

Another drawback of known clamps lies in their having to be discarded together with the disposable kit as a whole, with no possibility of being salvaged for further use.

DISCLOSURE OF INVENTION

According to the present invention, there is provided a fast-fit clamp for partly or fully closing flexible tubes, in particular for medical use, the clamp comprising a laminar body bent backwards on itself, fitted through longitudinally with a tube, and having two elastically competing ends between which project radially inwards two opposite transverse teeth for gripping the tube; characterized in that at least two split through holes are formed in said laminar body, with openings facing outwards on opposite sides; and provision being made for centering means for centering the competing ends, and latch means for fastening said competing ends.

BRIEF DESCRIPTION OF DRAWINGS

A preferred, non-limiting embodiment of a fast-fit clamp for regulating flow along flexible tubes, in particular for medical use, will be described by way of example with reference to the accompanying drawings, in which:

FIG. 1 shows a view in perspective of the clamp according to the invention being fitted to a tube;

FIG. 2 shows the clamp according to the invention with the tube inserted and about to grip the tube;

FIG. 3 shows a possible embodiment of means for gradually fastening the ends of the clamp.

BEST MODE FOR CARRYING OUT THE INVENTION

With reference to the accompanying drawings, number 1 indicates a fast-fit clamp for regulating flow along a flexible tube 2, in particular for medical use.

Clamp 1 is substantially defined by a laminar body 3, which is bent backwards on itself, is fitted through longitudinally with tube 2, and has two elastically competing ends 3a and 3b, between which project radially inwards two opposite transverse gripping teeth 4 for gripping tube 2.

Laminar body 3 thus achieves, as seen In a median longitudinal cross-section plane, a substantially U-shaped configuration with an elastic bent region comprised between two opposite arms ending with the ends 3a, 3b. The body 3 further comprises at least two split through holes 5 and 6 having respective slotted openings 5a and 6a, extending each through an opposite side edge of the body 3 and facing outwards on opposite sides with respect to the median longitudinal cross-section plane so as to allow edgewise insertion of the tube 2 in the openings 5 and 6.

The laminar body 3 also comprises centering means 7 for centering competing ends 3a and 3b; and latch means 8 for fastening competing ends 3a and 3b and so gripping tube 2.

Openings 5a and 6a are advantageously slightly smaller than the diameter of tubes 2 used, so as to retain the tubes in position once clamp 1 is fitted on.

Means 7 for centering competing ends 3a and 3b are defined by at least one longitudinal centering tooth 9 projecting from the bottom face of one of said ends-in the example shown, end 3a and which engages a corresponding hollow seat 10 formed longitudinally in the top face of competing end 3b; and tooth 9 and hollow seat 10 have complementary sections for achieving and maintaining a precise prismatic fit.

The pressure point P on which finger pressure is applied to fasten the clamp projects with respect to the superimposed transverse teeth 4, so as to increase the lever arm B of the force applied manually.

Latch means 8 comprise a latching surface 11 formed transversely from a platform 12 projecting from one of the competing ends-in the example shown, end 3b-and which is engaged underneath, by a transverse latching tooth 13 projecting from competing end 3a.

If necessary, competing ends 3a and 3b of clamp 1 may be fastened gradually; in which case, surface 11 is replaced with a number of parallel, superimposed surfaces 11a, each, with the exception of the top one, having a sot 14 for the passage of tooth 9.

Operation of the invention is self-explanatory from the foregoing description: to apply clamp 1, the user fits the clamp wherever required crosswise to tube 2 with ends 3a and 3b open, and then turns the clamp-e. g. anticlockwise in the accompanying drawings-to insert tube 2 inside holes 5 and 6 by forcing the tube slightly through opposite openings 5a and 6a.

The deliberately small size of openings 5a and 6a with respect to the diameter of tube 2 provides for retaining the tube inside holes 5 and 6 even when clamp 1 is open.

The user then applies finger pressure at point P to fasten end 3a to 3b in opposition to the elasticity of body 3 and with very little effort on account of the extensive lever arm B.

To fasten the clamp, tooth 13 engages the underside of surface 11, and tooth 9 is automatically centered inside hollow seat 10 to keep ends 3a and 3b of body 3 transversely integral with each other.

When the clamp is closed, teeth 4 close tube 2 completely; and, to choke the tube, tooth 13 may engage the underside of one of superimposed surfaces 11a so that teeth 4 only partly close the section of tube 2 by a predetermined amount.

The invention described has proved successful in achieving the objects proposed.

Clearly, changes may be made to the invention as described herein without, however, departing from the scope of the invention itself.

All the details may be replaced by others technically equivalent.

Any materials, shaped and sizes may be employed as required, without departing from the scope of the accompanying Claims.

What is claimed is:

1. A fast-fit clamp for partly or fully closing a flexible tube, comprising:
    a laminar elongated body bent backwards on itself so as to achieve, in a cross-section median longitudinal plane, a substantially U-shaped configuration, said laminar body comprising an elastic bent region provided between two opposite arms, said arms having opposite ends which are movable, by finger pressure, from a normally spaced apart configuration to a closed configuration in which said ends arc fastened to each other;
    at least two through holes formed in said laminar body at a first one of said ends and at said bent region, respectively, said through holes being adapted for fitting therein the flexible tube;
    opposite gripping teeth, projecting towards each other from a respective one of said arms for gripping the tube fitted in said through holes;
    slotted openings, extending each through an opposite side edge of said laminar body at said through holes so as to allow edgewise insertion of the tube in each of said through holes from an opposite side with respect to said median longitudinal cross-section plane;
    centering means for centering said opposite ends upon fastening thereof in said closed configuration that comprise at least one centering tooth projecting from a bottom face of a first one of said arm ends and a corresponding hollow seat formed at a top face of a second one of said arm ends, said centering tooth being engageable in said hollow seat; and
    latch means provided at said opposite arms for fastening to each other said opposite ends, wherein said latch means comprises gradual fastening means that include a latching tooth and a plurality of parallel, superimposed latching surfaces provided each at a respective one of said arm ends, and wherein said parallel, superimposed latching surfaces comprise all but for a top one, a slot that extends theretrough for allowing passage of said centering tooth upon closure of the clamp.

2. The clamp of claim 1, wherein said slotted openings have a cross sectional dimension which is slightly smaller than a diameter of the tube to be inserted in said through holes so as to retain the tube in position once the clamp is fitted thereon.

3. The clamp of claim 1, wherein said centering tooth and said hollow seat have complementary cross-section shapes.

4. The clamp of claim 1, further comprising a pressure point on which finger pressure is applicable for closing the clamp, said pressure point being provided at said first arm end in a region thereof that projects with respect to said gripping teeth for increasing lever arm for a closure force applied by finger pressure.

5. The clamp of claim 1, wherein said latch means is constituted by a mechanical connection comprising a latching tooth and a latching surface, each of which is provided at a respective one of said arm ends and so as to project towards each other, said latching tooth engaging an underside region of said latching surface upon closure of the clamp.

6. The clamp of claim 1, being a fast-fit clamp for medical use.

* * * * *